(12) United States Patent
Vale et al.

(10) Patent No.: US 6,831,160 B1
(45) Date of Patent: Dec. 14, 2004

(54) METHOD OF AFFINITY PURIFYING PROTEINS USING MODIFIED BIS-ARSENICAL FLUORESCEIN

(75) Inventors: Ronald D. Vale, San Francisco, CA (US); Kurt Thorn, San Francisco, CA (US); Roger Cooke, San Francisco, CA (US); Marija Matsuka, San Francisco, CA (US); Nariman Naber, San Bruno, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/502,664

(22) Filed: Feb. 11, 2000

Related U.S. Application Data

(60) Provisional application No. 60/178,054, filed on Jan. 24, 2000.

(51) Int. Cl.[7] ................................................. A23J 1/00
(52) U.S. Cl. ...................... 530/412; 530/412; 530/350; 530/300; 435/69.1; 435/7.9; 435/7.1; 549/207; 568/411; 562/324
(58) Field of Search ..................... 549/207; 568/411; 562/324; 435/69.1, 7.9, 7.1; 530/300, 350, 412

(56) References Cited

U.S. PATENT DOCUMENTS

| | | | |
|---|---|---|---|
| 5,264,557 A | 11/1993 | Salomon et al. ............ 530/399 |
| 5,415,999 A | 5/1995 | Saul et al. ................... 435/709 |
| 5,932,474 A | 8/1999 | Tsien et al. ............... 435/320.1 |
| 6,008,378 A | * 12/1999 | Tsien et al. .................. 549/207 |

OTHER PUBLICATIONS

Griffin et al., Science, vol. 281, pp. 269–272, 1998.*

Griffen, B. Albert, "Specific Covalent Labeling of Recominant Protein Molecules Inside Live Cells," Science, vol. 281, Jul. 10, 1998, pp. 269–272.

Luebke, Kevin J., "A FLASH of Insight into Cellular Chemistry: Genetically Encoded Labels for Protein Visualization In Vivo," Chemistry & Biology, vol. 5, No. 12, 1998, pp. R317–R322.

* cited by examiner

Primary Examiner—Christopher S. F. Low
Assistant Examiner—Hope A. Robinson
(74) Attorney, Agent, or Firm—Gray Cary Ware & Freidenrich, LLP

(57) ABSTRACT

The present invention features methods for purifying polypeptides of interest using a modified Fluorescein arsenical helix binder (FlAsH) compound immobilized on a solid support. An exemplary FlAsH target sequence motif is also presented. Examples of modification of the FlAsH compound which allow immobilization to a solid support are also provided. The present invention also provides DNA constructs for producing a dual affinity tagged polypeptide and methods for purification thereof.

19 Claims, 1 Drawing Sheet

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial sequence
<220> FEATURE:
<223> OTHER INFORMATION: FlAsH target sequence motif
<221> NAME/KEY: Variant
<222> LOCATION: (1)..(6)
<223> OTHER INFORMATION: Xaa is any Amino Acid

<400> SEQUENCE: 1

Cys Cys Xaa Xaa Cys Cys
1               5

<210> SEQ ID NO 2
<211> LENGTH: 17
<212> TYPE: PRT
<213> ORGANISM: Artificial sequence
<220> FEATURE:
<223> OTHER INFORMATION: FlAsH-tag peptide

<400> SEQUENCE: 2

Trp Glu Ala Ala Ala Arg Glu Ala Cys Cys Arg Glu Cys Cys Ala Arg
1               5                   10                  15

Ala
```

METHOD OF AFFINITY PURIFYING PROTEINS USING MODIFIED BIS-ARSENICAL FLUORESCEIN

RELATED APPLICATIONS

This application claims priority under 35 USC 119(e)(1) to U.S. Provisional Patent application Ser. No. 60/178,054, filed Jan. 24, 2000, incorporated herein in its entirety.

GOVERNMENT SUPPORT

This invention was made with Government support under Grant No. AR42895, awarded by the National Institutes of Health. The Government may have certain rights in this invention.

FIELD OF THE INVENTION

This invention relates generally to affinity purification of proteins and more specifically to the use of a modified bis-arsenical fluorescein compound immobilized to a solid support for protein purification.

BACKGROUND OF THE INVENTION

Many techniques in the biological sciences require attachment of labels to molecules, such as polypeptides. For example, the location of a polypeptide within a cell can be determined by attaching a fluorescent label to the polypeptide.

Traditionally, labeling has been accomplished by chemical modification of purified polypeptides. For example, the procedures for fluorescent labeling require that the polypeptide be covalently reacted in vitro with a fluorescent dye, then repurified to remove excess dye and/or any damaged polypeptide. Using this approach, problems of labeling stoichiometry and disruption of biological activity are often encountered. Furthermore, to study a chemically modified polypeptide within a cell, microinjection can be required. This can be tedious and cannot be performed on a large population of cells.

Thiol- and amine-reactive chemical labels exist and can be used to label polypeptides within a living cell. However, these chemical labels are promiscuous. Such labels cannot specifically react with a particular cysteine or lysine of a particular polypeptide within a living cell that has numerous other reactive thiol and amine groups.

A more recent method of intracellular labelling of polypeptides in living cells has involved genetically engineering fusion polypeptides that include green fluorescent protein (GFP) and a polypeptide of interest. However, GFP is limited in versatility because it cannot reversibly label the polypeptide. The ability to generate a wide range of specifically labeled molecules easily and reliably would be particularly useful.

The use of genetically-encoded affinity tags is now a standard method of purifying proteins (reviewed in (Hannig and Makrides, 1998; LaVallie and McCoy, 1995; Makrides, 1996; Nilsson, et al., 1997 ; Uhlén and Moks, 1990)). This technique allows for simple purification of a protein of interest by fusing to it a tag with affinity for a stationary phase. Most affinity tags are small-molecule binding proteins (e.g. maltose binding protein, glutathione S-transferase). However, the size of these proteins can potentially interfere with the protein to which they are fused. A few short peptides, which are potentially less perturbing, have been used as affinity tags. The most common ones are the 6×histidine tag and the FLAG tag (a 6 amino acid antibody epitope). However, both these affinity tags have disadvantages. The FLAG tag requires the use of an expensive antibody affinity matrix and as a result has not received widespread use. The polyhistidine tag, which binds to metal ions, is very widely used, but requires somewhat harsh conditions (either high concentrations of imidazole or low pH) for elution, which can disrupt macromolecular complexes. In addition, small amounts of metal ions that elute with the protein can inactivate many enzymes. The purity of the eluted protein can be low because many histidine-rich proteins can bind to and elute from metal affinity resins, contaminating the purified protein.

Recently, a fluorescent dye has been developed which specifically interacts with tetracysteine containing helices (Griffin, et al., Science 281:269–272 (1998)). This compound, known as FlAsH (fluorescein arsenical helix binder), has been shown to specifically interact with proteins tagged with a C-C-$X_1$-$X_2$-C-C containing helix. The interaction is readily reversed by incubation with small dithiols such as ethanedithiol. FlAsH affinity chromatography is a highly specific protein purification method. It is based on the regiospecific interaction of two arsenics in FlAsH with two pairs of cysteines in a target alpha helix. The only requirement for binding is that the protein of interest contain the motif C-C-$X_1$-$X_2$-C-C within an alpha helix. This motif is rarely found in proteins, and labeling tagged proteins in vivo (Griffin, et al., Science 281:269–272 (1998)) indicate that there are very few eukaryotic proteins that bind to FlAsH. In contrast, many organisms contain histidine-rich proteins, and binding of these proteins to metal ion resins is a major source of contamination.

SUMMARY OF THE INVENTION

The present invention is based on the discovery of a method for protein purification using a modified fluorescein arsenical helix binder (FlAsH) compound, immobilized to a solid support, which can yield substantially pure protein from a single purification step.

A particularly preferred modified bis-arsenical molecule of the invention has the following formula:

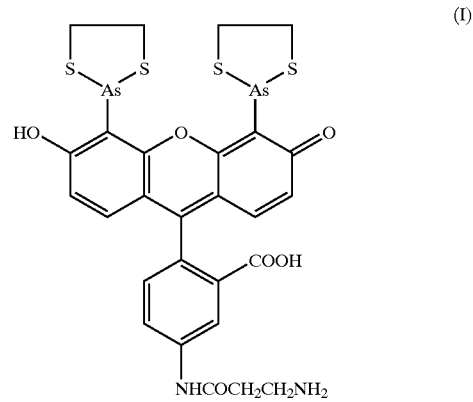

The tautomers, anhydrides and salts of the modified bis-arsenical molecule of formula (I) are also included.

Preferably, the modified bis-arsenical molecule specifically reacts with a target sequence, within the bonding partner, to generate a detectable signal, for example, a fluorescent signal.

The modified bis-arsenical molecule preferably is capable of traversing a biological membrane. The modified bis-arsenical molecule preferably includes a detectable group, for example a fluorescent group, luminescent group, phosphorescent group, spin label, photosensitizer, photocleavable moiety, chelating center, heavy atom, radioactive isotope, isotope detectable by nuclear magnetic resonance, paramagnetic atom, and combinations thereof.

In a first aspect, the invention includes a method for isolating a polypeptide of interest including contacting a modified Fluorescein Arsenical Helix (FlAsH) binder compound immobilized on a solid support with a sample containing a polypeptide of interest under conditions that allow binding of the polypeptide to the immobilized FlAsH compound, and eluting the polypeptide of interest, which has been modified by the addition of the FlAsH target sequence motif C-C-$X_1$-$X_2$-C-C (SEQ ID NO: 1,), where $X_1$ and $X_2$ are any amino acid, from the immobilized FlAsH compound. The polypeptide of interest which contains the FlAsH target sequence is the bonding partner of the modified FlAsH compound. "Bonding partner" as used herein refers to a molecule that contains at least the target sequence.

Another aspect of the invention provides a DNA construct containing an origin of replication, a selectable marker, a promoter that allows expression of the polypeptide of interest, and a cloning site, wherein the 5' end of the cloning site contains a genetically-encoded affinity tag, and wherein the 3' end of the cloning site contains a FlAsH target sequence motif.

Yet another aspect of the invention provides a DNA construct comprising an origin of replication, a selectable marker, a promoter that allows expression of the polypeptide of interest, and a cloning site, wherein the 5' end of the cloning site contains a FlAsH target sequence motif, and wherein the 3' end of the cloning site contains a genetically-encoded affinity tag.

Still another aspect of the invention provides a method for producing a polypeptide of interest which contains at its N-terminus a genetically-encoded affinity tag and at its C-terminus contains a FlAsH target sequence motif including, expressing a DNA sequence which encodes the polypeptide of interest as in the above-mentioned DNA construct, in an appropriate cell type, and producing the polypeptide of interest in an appropriate cell type.

Another aspect of the invention provides a method for isolating a polypeptide of interest, wherein the polypeptide contains at its N-terminus a genetically encoded affinity tag and at its C-terminus a FlAsH sequence motif. The method includes contacting a sample which contains a polypeptide of interest with an affinity resin which binds to the affinity tag; eluting the polypeptides bound to the affinity resin; contacting a modified FlAsH compound immobilized on a solid support with the polypeptides eluted from the first affinity resin, under conditions that allow binding of the polypeptide to the FlAsH compound; and eluting the polypeptide of interest from the immobilized FlAsH compound.

Still another aspect of the invention provides a method for isolating a polypeptide of interest, wherein the polypeptide contains at its N-terminus a genetically-encoded affinity tag and at its C-terminus a FlAsH sequence motif including: contacting a sample which contains a polypeptide of interest with a FlAsH compound immobilized to a solid support; eluting the polypeptides bound to the immobilized FlAsH compound; contacting an affinity resin with the polypeptides eluted from the FlAsH affinity resin, under conditions that allow binding of the polypeptide to the second affinity resin; and eluting the polypeptide of interest from the second affinity resin.

Another aspect of the invention provides a method for producing a polypeptide of interest containing at its N-terminus a FlAsH target sequence motif and at its C-terminus a genetically-encoded affinity tag. The method includes expressing a DNA sequence which encodes a polypeptide of interest from the DNA constructs of the present invention which allow addition of either the FlAsH target sequence motif or another genetically-encoded affinity tag, in an appropriate cell type, and producing the polypeptide of interest, modified to contain affinity tags, in the appropriate cell type.

Yet another aspect of the invention provides a method for isolating a polypeptide of interest, containing at its N-terminus a FlAsH target sequence motif and at its C-terminus a genetically-encoded affinity tag. The method includes contacting a sample which contains a polypeptide of interest with an affinity resin which binds to the affinity tag; eluting the polypeptides bound to the affinity column; contacting a modified FlAsH compound immobilized on a solid support with the polypeptides eluted from the affinity resin, under conditions that allow binding of the polypeptide to the FlAsH compound; and eluting the polypeptide of interest from the immobilized FlAsH compound.

Another aspect of the invention provides a method for isolating a polypeptide of interest, which has at its N-terminus a FlAsH target sequence motif and at its C-terminus a genetically-encoded affinity tag. The method includes contacting a sample which contains a polypeptide of interest with a FlAsH compound immobilized to a solid support; eluting the polypeptides bound to the immobilized FlAsH compound; contacting an affinity resin with the polypeptide eluted from the immobilized FlAsH compound, under conditions that allow binding of the polypeptide to the affinity resin; and eluting the polypeptide of interest from the affinity resin.

In yet another aspect, the invention features a kit that includes all the materials and reagents to carry out the invention as described for both FlAsH affinity purification or dual affinity tag purification. A kit of the invention includes at least a modified FlAsH compound as described herein.

DESCRIPTION OF THE PREFERRED EMBODIMENTS

Figure 1:
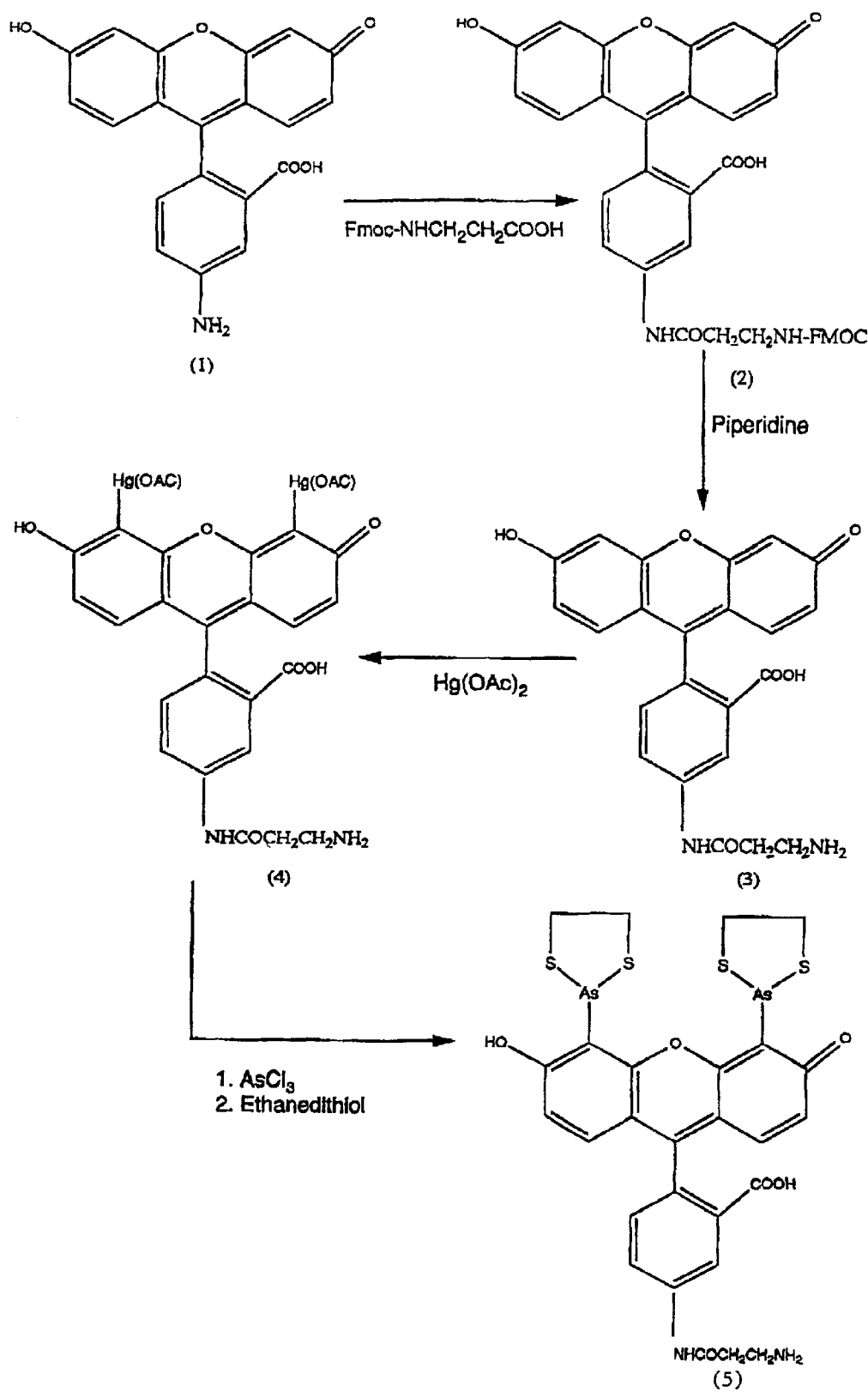
FIG. 1: Synthesis of 4'5'-bis(1,2,3-dithioarsolan-2yl)5-((5-aminoethyl)aminocarbonyl-fluorescein (β-alanyl FlAsH). Aminofluorescein was modified to contain a primary amine in the 5 position to allow attachement to an NHS-functionalized stationary phase. This was done by acylating aminofluorescein (1) with β-alanine. The β-alanyl Fluorescein (2) was then converted to the bis-arsenical derivative (5). The final compound, referred to as Formula (I), was then used for protein purification.

This invention relates to methods and compounds for affinity purification of proteins using a modified bis-arsenical fluorescein compound immobilized to a solid support. The invention also provides nucleic acid constructs for use in adding genetically-encoded affinity tags to polypeptides. The invention also provides kits which include all components necessary to practice the invention.

The present invention provides modified bis-arsenical molecules having the formula described in Formula (I). The present invention also includes tautomers, anhydrides and salts of the modified bis-arsenical molecule. FIG. 1 illustrates a method for generation of the FlAsH compound of the invention which is useful for immobilization to a solid support. "Wild-type" or "unmodified" bis-arsenical molecules are described in detail in U.S. Pat. No. 6,008,378, herein incorporated by reference in its entirety.

FlAsH affinity chromatography has a number of desirable features. An affinity tag (C-C-$X_1$-$X_2$-C-C, wherein $X_1$ and $X_2$ are any amino acid, SEQ ID NO: 1) can be attached at either the N- or C-terminus of the protein or can be incorporated into an existing helix within the protein. The ability to incorporate the FlAsH target sequence motif into an existing structural element within a protein has proven difficult with other affinity tags. The FlAsH affinity tag has been shown to not interfere with kinesin function and will not perturb the function of other proteins when added at either terminus.

A FlAsH resin is compatible with many commonly used buffer components. Buffers containing primary amines (e.g. Tris) and divalent metal chelators, both of which interfere with Ni-resin purifications, are fully compatible with FlAsH. The FlAsH-peptide interaction is also stable to 1 M NaCl, which would allow proteins bound to the polypeptide of interest which in turn is bound to the FlAsH resin, to be eluted by conventional chromatographic techniques. An example of this would be elution of accessory transcription factors bound to a polypeptide of interest which is bound to the FlAsH resin.

Reducing agents containing a single thiol, such as γ-mercaptoethanol, can be used in concentrations up to at least 5 mM, and dithiothreitol can be included at concentrations up to 1 mM without interfering with protein binding to the FlAsH resin. The elution of tagged proteins from FlAsH resins occurs under conditions, which do not interfere with the function of the polypeptide of interest. Bound proteins are eluted by millimolar concentrations of a dithiol (EDT, DMPS or DIT), which are unlikely to perturb protein structure or protein-protein interactions. In contrast, many other purification methods require changes in ionic strength or pH for elution, which could alter the conformation or functionality of the protein. This gentle elution of bound protein makes FlAsH affinity chromatography ideal for purification of macromolecular complexes.

The high affinity and regiospecificity of the modified FlAsH target sequence interaction raises the potential for the use of this technique for attaching tagged proteins onto the surface of a bead or coverslip in a site-specific and oriented manner. This could be useful for functional assays of protein arrays on surfaces.

A modified bis-arsenical molecule of the invention may be engineered to contain a variety of detectable groups. "Detectable group" as used herein refers to any atom or molecule that can be engineered into the bis-arsenical molecule to aid in the detection of the bis-arsenical molecule without significantly destroying the modified bis-arsenical molecule's ability to react with a target sequence.

A modified bis-arsenical molecule of the invention may be substituted at one or more positions to add a signal generating detectable group. Inclusion of more than one detectable group is also within the scope of this invention. The selection of a detectable group may be made based on the ease of the protocol for engineering the detectable group into the modified bis-arsenical molecule, and on the end use of the modified bis-arsenical molecule. Examples of detectable groups include fluorescent groups, phosphorescent groups, luminescent groups, spin labels, photosensitizers, photocleavable moieties, chelating centers, heavy atoms, radioactive isotopes, isotopes detectable by nuclear magnetic resonance, paramagnetic atoms, and combinations thereof.

Typically, a detectable group generates a detectable signal that can be readily monitored. Examples of detectable signals that can be monitored include fluorescence, fluorescence anisotropy, time-resolved luminescence, phosphorescence amplitude and anisotropy, electron spin resonance (ESR), singlet oxygen production, hydroxy radical-mediated protein inactivation, metal-ion sensing, X-ray scattering, radioactivity, nuclear magnetic resonance spectroscopy of the attached isotope, and enhanced relaxivity of protons in the immediate vicinity of a paramagnetic species.

Other modifying groups that aid in the use of a modified bis-arsenical molecule may also be incorporated. For example, the modified bis-arsenical molecule of the invention may be substituted at one or more positions to add a solid phase binding group or a cross-linking group. The modified bis-arsenical molecule may be coupled to a solid phase.

A modified bis-arsenical molecule of the invention preferably is capable of traversing a biological membrane. The small size of the bis-arsenical molecule can contribute toward the ability of the bis-arsenical molecule to traverse a biological membrane. bis-arsenical molecules of less than 800 Daltons are preferable for membrane traversal.

A modified bis-arsenical molecule of the invention may also lack a detectable signal, both before and even after specifically reacting with a target sequence. These modified bis-arsenical molecules can be useful in many techniques that do not require a detectable signal, or that use other methods of detection. These modified bis-arsenical molecules may be useful when the goal is to attach a polypeptide to a solid substrate, cross-link two polypeptides or encourage a polypeptide domain to become α-helical.

Each of the two trivalent arsenics in the modified bis-arsenical molecule of the invention may react with a pair of adjacent cysteines. Thus, the modified bis-arsenical molecule may specifically react with four cysteines arranged in an appropriate configuration.

A particularly useful advantage of the specific reaction between the modified bis-arsenical molecule of the invention and a target sequence is the reversibility of the reaction. A complex containing the modified bis-arsenical molecule and the target sequence may be dissociated. Dissociation may be accomplished by providing an excess of reagents such as EDT as discussed in Example 2 below or other similar dithiols.

"Tetraarsenical" molecules as used herein refer to molecules that contain four arsenics. In some embodiments, tetraarsenical molecules are two modified bis-arsenical molecules chemically coupled to each other through a linking group. Tetraarsenical molecules may be synthesized in a variety of ways, as described in U.S. Pat. No. 6,008,378.

In a preferred embodiment, a polypeptide of interest is modified to contain the FlAsH target sequence motif, C-C-$X_1$-$X_2$-C-C (SEQ ID NO: 1), where $X_1$ and $X_2$ represent any amino acid. $X_1$ and $X_2$ can represent either the same or different amino acids, or can represent amino acids that have a high α-helical propensity.

Generally, a target sequence includes one or more cysteines, preferably four, that are in an appropriate configuration for reacting with a modified bis-arsenical molecule. A target sequence alone may be able to react with a modified bis-arsenical molecule. A target sequence can vary in size. Typically it contains at least 6 amino acids. Preferably, the target sequence is at least 10 amino acids. Alternatively, a target sequence may only adopt an appropriate configuration when it is associated with a carrier molecule. For example, a modified bis-arsenical molecule of the invention may react with a target sequence only when the target sequence is placed in an α-helical domain of a polypeptide.

A target sequence may have an amino acid sequence such that two pairs of cysteines are arranged to protrude from the same face of an α-helix. Preferably, the four sulfurs of the cysteines form a parallelogram.

A target sequence alone may not be completely helical under the reaction conditions. For example, reaction of a first arsenic with a pair of cysteines may nucleate an α-helix and position the two other cysteines favorably for reacting with the other arsenic of the bis-arsenical molecule.

Formation of an α-helix may also be favored by incorporation of oppositely charged amino acids that are separated by about three amino acids. These oppositely charged amino acids may be properly placed to form salt bridges across one turn of an α-helix. An example of a pair of oppositely charged amino acids is arginine and glutamate. Merutka & Stellwagen., *Biochemistry* 30: 1591–1594 and 4245–4248 (1991). It is preferable to position glutamate toward the N-terminus of the α-helix and arginine toward the C-terminus for favorable interaction with the dipole of an α-helix. The N-terminus of the target sequence may be acetylated. The C-terminus of the target sequence may be amidated.

A target sequence containing other secondary structures is also within the scope of this invention. For example, the one or more cysteines of the target sequence may be within a β-sheet structure. Other secondary structures are possible as long as the target sequence can react with the bis-arsenical molecule.

An example of a target sequence is SEQ ID NO. 1, as well as variants thereof that retain reactivity with the bis-arsenical molecule. "Variant" target sequences contain one or more amino acid substitutions, typically with amino acid substitutes of approximately the same charge and polarity. Such substitutions can include, e.g., substitutions within the following groups: valine, isoleucine, leucine, methionine; aspartic acid, glutamic acid; asparagine, glutamine; serine, threonine; lysine, arginine; and phenylalanine, tyrosine. In general, such substitutions do not significantly affect the function of a polypeptide. Methods for producing target sequences include molecular biology methods and chemical polypeptide synthesis methods.

A FlAsH target sequence can be located at either the N- or C-terminus of the protein or can be incorporated in any region within the protein that is α-helical in nature and accessible to the surrounding environment, so long as protein function is not altered. The sequence can be added using a variety of recombinant DNA techniques including, but not limited to, nucleic acid vectors used to express polypeptides which contain an appropriate FlAsH target DNA sequence either 5' or 3' to a multiple cloning site into which a DNA sequence which encodes a polypeptide of interest is inserted, DNA linkers which can be added to a DNA sequence which encodes a polypeptide of interest prior to incorporating the DNA sequence into an appropriate expression vector, and site directed mutagenesis of an existing α-helical domain in the polypeptide of interest such that the resultant polypeptide of interest contains the FlAsH target sequence. Other recombinant DNA methods useful for adding the FlAsH target sequence to a polypeptide of interest are also within the scope of the invention, and will be apparent to those of skill in the art.

In one embodiment of the invention, $X_1$ and $X_2$ represent the same amino acid. In another embodiment of the invention, $X_1$ and $X_2$ represent different amino acids. In the preferred embodiment, the amino acids have a high α-helical propensity. Amino acids that have a high α-helical propensity include alanine, leucine, methionine, and glutamate, for example.

In another embodiment of the invention, a wild-type FlAsH compound is modified to contain a primary amine at the 5 position of the fluorescein in order to produce the preferred modified FlAsH compound of the invention. This can be accomplished by acylating amino-fluorescein with an amino acid. Following cleavage of the protecting group, the amino-acyl-amino-fluorescein is then converted to the mercuric acetate derivative (Karush, et al., An assay method for optimizing heterologous protein expression in *Eschericia coli*. Anal. Biochem. 9:100–114 (1964); Shipchandler and Fino, A revised structure of fluorescein mercuric acetate. Anal. Biochem. 154:476–477 (1986)) and then to the bis-arsenical derivative by transmetallation as described for synthesis of the original FlAsH compound (Griffin, et al., Specific covalent labelling of recombinant protein molecules inside live cells. Science 281:269–272 (1998), see FIG. 1, see also U.S. Pat. No. 6,008,378).

In a preferred embodiment, the amino-fluorescein is acylated using β-alanine. The active compound, β-alanyl FlAsH, has very similar spectroscopic properties to the previously described FlAsH compound (Griffin, et al., Science 281:269–272 (1998), see FIG. 1, see also U.S. Pat. No. 6,008,378). The primary amine on the β-alanyl FlAsH readily reacts with an N-hydroxysuccinamide (NHS)-functionalized stationary phase to give a stable covalent linkage. The advantage of the modified FlAsH compound described herein is its usefulness in protein purification as well as the potential for use in functional assays of protein arrays by attaching tagged proteins onto the surface of beads or coverslips in a site-specific and oriented manner.

The modified fluorescein bis-arsenical compound is then preferably conjugated to a solid support matrix. Examples of materials that can be used as a suitable solid support matrix on which to immobilize the modified FlAsH compound included, but are not limited to, agarose, polyacrylimide, glass, ceramics, natural or synthetic polymeric materials, beads, coverslips, paper, metals, metalloids, polacryloylmorpholide, various plastics and plastic copolymers such as Nylon™, Teflon™, polyethylene, polypropylene, poly(4-methylbutene), polystyrene, polystyrene, polystyrene/latex, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and controlled-pore glass (Controlled Pore Glass, Inc., Fairfield, N.J.), aerogels (see e.g., Ruben et al., J. Materials Science 27, 4341–4349 (1992); Rao et al., J. Materials Science 28, 3021 (1993); Back et al., J. Phys. D. Appl. Phys. 22, 7309 (1989); Kim and Jang, J. Am Ceram. Soc. 74, 1987–1992 (1991)), affinity exchange resins, and other materials generally known to one skilled in the art to be suitable for use in affinity columns. In the most preferred embodiment, the β-alanyl FlAsH is reacted with N-hydroxysuccinamide (NHS)-functionalized agarose beads.

Affinity chromatography is a highly specific protein purification method. It is based on the regiospecific interaction of two arsenics in FlAsH with two pairs of cysteines in a target alpha helix. The only requirement for binding is that the protein of interest contain the motif $C-C-X_1-X_2-C-C$ (SEQ ID NO: 1) within an alpha helix. Thus, to purify a protein of interest using the FlAsH affinity chromatography technique it is first necessary to modify the polypeptide of interest so that it contains the target sequence motif, C-C-$X_1$-$X_2$-C-C (SEQ ID NO: 1). Constructs developed for this purpose are described below.

One of the advantages of the protein purification using the immobilized FlAsH compound, is that it can be adapted for use in many different types of chromatography. The types of chromatography known to one of skill in the art are numerous and include, but are not limited to, batch elution, FPLC, HPLC, affinity chromatography, and gel filtration.

Typically, a sample which contains a polypeptide of interest is obtained from a cell lysate, crude polypeptide extract, or a partially purified polypeptide extract. The lysate or extracts can be made from cells or cell free solutions derived from any organism or cell type, for example, plants, prokaryotes, or eukaryotes.

The sample containing a polypeptide of interest is contacted with the FlAsH affinity resin in a manner that allows the polypeptide of interest to be bound. One of skill in the art of protein purification will realize that the conditions required for binding of a polypeptide of interest will vary according to the nature of polypeptide being purified.

Polypeptides of interest are purified by binding of the immobilized FlAsH compound with a FlAsH target sequence, C-C-$X_1$-$X_2$-C-C (SEQ ID NO: 1), contained in the polypeptide of interest, followed by elution from the immobilized FlAsH compound with a dithiol solution. The FlAsH target sequence motif can be located at either the N-terminus or the C-terminus of the protein, or in any region of the protein that is α-helical in nature and accessible to the surrounding environment.

In one embodiment of the invention, Batch affinity purification is performed. For this technique, the sample containing a polypeptide of interest is contacted with the FlAsH affinity resin for a period of time that will allow binding of the polypeptide of interest to the immobilized FlAsH compound. One of skill in the art will understand that many different methods may be used for contacting the immobilized FlAsH compound with the polypeptide of interest. One of skill in the are will also realize that the period of time necessary for binding the polypeptide of interest to the FlAsH compound may vary, but will most likely fall in the range of between 1 and 24 hours at a temperature of between 4 and 8 degrees centigrade.

In another embodiment of the invention, column chromatography purification is used to isolate a polypeptide of interest. In this technique, a sample containing a polypeptide of interest is contacted with a solid support containing an immobilized FlAsH compound of the invention, followed by washing the support with a standard column buffer. An example of a buffer that is commonly used as a loading and wash buffer, is buffer A (25 mM PIPES, 2 mM $MgCl_2$, 1 mMEGTA, 0.1 mM ATP, 5 mM βME). The support is washed until the absorbance of the wash buffer, monitored at an 280 nm ($A_{280}$), returns to baseline. Further washes can be performed with buffered solutions which contain low concentrations of a dithiotheritol (DTT). The polypeptide of interest is then eluted from the immobilized FlAsH compound.

Regardless of the type of chromatography used, a polypeptide of interest is eluted from the immobilized FlAsH compound by the use of a dithiol solution. The concentration of dithiol solution used varies according to the structure of the dithiol, and are discussed in the embodiments below.

In one embodiment of the invention, a polypeptide of interest is eluted from the FlAsH affinity resin by the use of a buffer containing 1,2-ethanedithiol (EDT). Concentrations of EDT useful for elution are in the range of about 1 mM to 20 mM. A preferred embodiment uses a concentration range of EDT between about 1 mM and 10 mM, and more preferably a range of about 5 mM to 10 mM EDT is used to elute the polypeptide of interest from the immobilized FlAsH compound.

In another embodiment of the invention, a polypeptide of interest is eluted from the FlAsH affinity resin by the use of a buffer containing dithiothreitol (DTT). Concentrations of DTT useful for elution are in the range of about 10 mM to 100 mM. A preferred embodiment uses a concentration range of DTT between about 20 mM and 80 mM, and more preferably a range of about 40 mM to 60 mM DTT is used to elute the polypeptide of interest from the immobilized FlAsH compound.

In one embodiment of the invention, a polypeptide of interest is eluted from the FlAsH affinity resin by the use of a buffer containing 2,3-dimercaptopropanesulfonate (DMPS). Concentrations of DMPS useful for elution are in the range of about 1 mM to 20 mM. A preferred embodiment uses a concentration range of DMPS between about 1 mM and 10 mM, and more preferably a range of about 5 mM to 10 mM DMPS is used to elute the polypeptide of interest from the immobilized FlAsH compound. DMPS is the dithiol of choice because it shows no oxidation or aggregation of the eluted polypeptide, causes no precipitation of the eluted polypeptide, and has no unpleasant odor.

In still another aspect of the invention, polypeptides labeled with both a FlAsH target sequence and another genetically encoded affinity tag are purified using a two-step affinity purification scheme which would yield highly purified polypeptides. Examples of genetically encoded affinity tags include but are not limited to, polyhistidine (i.e., 6×His), maltose binding protein, glutathione S-transferase, and the FLAG tag. DNA constructs useful for creating polypeptides of interest which contain both a FlAsH target motif and another affinity tag are discussed below.

In one embodiment of the invention, a polypeptide of interest, which has been modified to include the FlAsH target sequence and another genetically encoded affinity tag, is contacted with a FlAsH compound immobilized to a solid support. The polypeptide is then eluted from the FlAsH compound using a dithiol solution. The eluate is then contacted with another support which has the bonding partner for the second affinity tag contairied on the polypeptide, such that the polypeptide can be further purified using the second affinity tag. The polypeptide is eluted from the second affinity column using a reagent suitable for dissociating the bound polypeptide from the affinity resin.

Another embodiment of the invention uses the genetically encoded affinity tag to partially purify the polypeptide of interest from a protein extract, followed by a subsequent further purification using the FlAsH affinity resin. The polypeptide of interest would be substantially pure following the two rounds of affinity purification.

Any of the polypeptides and/or target sequences used in the invention, collectively referred to herein as "polypeptides", can be synthesized by such commonly used methods as t-BOC or FMOC protection of a-amino groups. Both methods involve stepwise syntheses whereby a single amino acid is added at each step starting from the C terminus of the peptide (See, Coligan, et al., *Current Protocols in Immunology*, Wiley Interscience, 1991, Unit 9). Polypeptides may also be synthesized by the well known solid phase peptide synthesis methods described in Merrifield, (*J. Am.*

Chem. Soc., 85:2149, 1962), and Stewart and Young, *Solid Phase Peptides Synthesis*, (Freeman, San Francisco, 1969, pp. 27–62), using a copoly(styrene-divinylbenzene) containing 0.1–1.0 mMol amines/g polymer. On completion of chemical synthesis, the polypeptides can be deprotected and cleaved from the polymer by treatment with liquid HF-10% anisole for about ¼–1 hours at 0° C. After evaporation of the reagents, the polypeptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous polypeptide or polypeptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Polypeptides may also be produced by the "native chemical" ligation technique which links together polypeptides (Dawson et al., *Science*, 266:776, 1994). Protein sequencing, structure and modeling approaches for use with a number of the above techniques are disclosed in Protein Engineering, loc. cit., and Current Protocols in Molecular Biology, Vols. 1 & 2, supra.

The polypeptides can also be non-polypeptide compounds that mimic the specific reaction and function of a polypeptide ("mimetics"). Mimetics can be produced by the approach outlined in Saragovi et al., *Science*, 253:792–795 (1991). Mimetics are molecules which mimic elements of polypeptide secondary structure. See, for example, Johnson et al., "Peptide Turn Mimetics", in Biotechnology and Pharmacy, Pezzuto et al., Eds., (Chapman and Hall, New York 1993). The underlying rationale behind the use of peptide mimetics is that the peptide backbone exists chiefly to orient amino acid side chains in such a way as to facilitate molecular interactions. For the purposes of the present invention, appropriate mimetics can be considered to be the equivalent of any of the polypeptides used in the invention.

Useful polypeptides may also be generated by nucleic acid techniques involving expression of nucleic acid sequences that encode the polypeptides. Polypeptides of the invention may also be generated that contain the necessary FlAsH target motif or another genetically-encoded affinity, or both, using nucleic acid techniques know to those of skill in the art. The term "vector" refers to a DNA construct, plasmid, virus or other vehicle known in the art that has been manipulated by insertion or incorporation of a nucleic acid sequence.

The expression of a desired nucleic acid molecule may occur through transient expression of the introduced polypeptide-encoding nucleic acid sequence. Alternatively, permanent expression may occur through integration of the introduced nucleic acid sequence into a host chromosome. Therefore the cells can be transformed stably or transiently. The term "host cell" may also include any progeny of a host cell. It is understood that all progeny may not be identical to the parental cell since there may be mutations that occur during replication. However, such progeny are included when the term "host cell" is used.

Typically, the vector that includes the nucleic acid sequence encoding the bonding partner is introduced into a host cell. Methods of stable transfer, meaning that the vector having the bonding partner encoding nucleic acid sequence is continuously maintained in the host, are known in the art.

The vector, with appropriate regulatory elements for expression in a host cell, can be constructed as described above.

The vector may be introduced into a host cell by any conventional method, including retroviral transduction, electroporation, calcium phosphate co-precipitation, biolistics and liposome-based introduction. See, for example, Ausubel et al., *Introduction of DNA Into Mammalian Cells*, in CURRENT PROTOCOLS IN a MOLECULAR BIOLOGY (John Wiley & Sons, Inc. 1995).

A variety of host cell-specific expression vector systems may be utilized to express polypeptides in a host cell. These include microorganisms such as bacteria transformed with recombinant bacteriophage DNA, plasmid DNA or cosmid DNA expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); or animal cell systems infected with recombinant virus expression vectors (e.g., retroviruses, adenovirus, vaccinia virus), or transformed animal cell systems engineered for stable expression. Polypeptides may require translational and/or post-translational modifications such as addition of carbohydrates. These modifications can be provided by a number of systems, e.g., mammalian, insect, yeast or plant expression systems.

Eukaryotic systems, and preferably mammalian expression systems, allow for proper post-translational modifications of expressed mammalian polypeptides to occur. Eukaryotic cells which possess the cellular machinery for proper processing of the primary transcript, glycosylation, phosphorylation, and advantageously, plasma membrane insertion of a polypeptide may be used as host cells.

Methods that are well known in the art can be used to construct vectors, including in vitro recombinant DNA techniques, synthetic techniques, and in vivo recombination/genetic techniques. (See, for example, the techniques described in Maniatis et al. 1989 Molecular Cloning A Laboratory Manual, Cold Spring Harbor Laboratory, N.Y.) A variety of host-expression vector systems may be utilized to express the polypeptide of interest. These include but are not limited to microorganisms such as bacteria transformed with T7-based expression vectors for expression (Rosenberg, et al., Gene, 56:125, 1987), recombinant bacteriophage DNA, plasmid DNA or cosmid DNA expression vectors containing the coding sequence for the polypeptide of interest; yeast transformed with recombinant yeast expression vectors containing the coding sequence for the polypeptide of interest; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence for the polypeptide of interest; insect cell systems infected with recombinant virus expression vectors (e.g., baculovirus based expression vectors) containing the coding sequence for the polypeptide of interest; or animal cell systems infected with the pMSXND expression vector for expression in mammalian cells (Lee and Nathans, J. Biol. Chem., 263:3521, 1988), recombinant virus expression vectors (i.e., retroviral vectors) containing the coding sequence polypeptide of interest, or transformed animal cell systems engineered for stable expression. Examples of retroviral vectors include Moloney murine leukemia virus, (MoMuLV), Harvey murine sarcoma virus (HaMuS-V), murine mammary tumor virus (MuMTV), and Rous Sarcoma Virus (RSV). Expression vectors suitable for in vitro expression may also be used.

The use of genetically-encoded affinity tags is now a standard method of purifying polypeptides (reviewed in (Hannig and Makrides, 1998 ; LaVallie and McCoy, 1995; Makrides, 1996; Nilsson, et al., 1997; Uhlén and Moks, 1990)). Generally, the vector from which the polypeptide of interest is expressed, includes a nucleic acid sequence encoding the target sequence. Typically, the nucleic acid sequence is a DNA sequence, although the nucleic acid can be an RNA sequence. The nucleic acid sequence can be any sequence that encodes a target sequence capable of reacting with the bis-arsenical molecule. This can include nucleic acid sequences that are degenerate variants of each other. By "degenerate variants" is meant nucleic acid sequences that encode the same amino acid sequence, but in which at least one codon in the nucleotide sequence is different. Degenerate variants occur due to the degeneracy of the genetic code, whereby two or more different codons can encode the same amino acid. Nucleic acid sequences of the present invention may be synthetic.

The vector may also contain a nucleic acid sequence encoding a polypeptide of interest, in addition to the nucleic acid sequence encoding the target sequence. Nucleic acid sequences encoding the polypeptide of interest and the target sequence can form a recombinant gene that, when expressed, produces a polypeptide bonding partner.

The nucleic acid sequence encoding the target sequence can be on the 5' or 3'-end of the nucleic acid sequence encoding the polypeptide of interest. Alternatively, the nucleic acid sequence encoding the target sequence can be internal to the nucleic acid sequence encoding the polypeptide of interest. In such a case, the nucleic acid sequence encoding the target sequence can be spliced into an internal site of the nucleic acid sequence encoding the polypeptide of interest. In this case, the nucleic acid sequence encoding the target sequence is flanked by nucleic acid sequences encoding the polypeptide of interest.

The nucleic acid sequence encoding the polypeptide of interest may contain an appropriate restriction enzyme site within its nucleic acid sequence that can be used for inserting the nucleic acid sequence encoding the target sequence. Alternatively, an appropriate restriction enzyme site can be engineered in the nucleic acid sequence encoding the polypeptide of interest at a desired location. A restriction enzyme site may be engineered by any number of known methods.

The nucleic acid sequence encoding the polypeptide of interest may by altered at one or more positions to generate the nucleic acid sequence that encodes the target sequence. For example, kinesin can be altered to create a target sequence as described in Example 2. In some embodiments, changes in the nucleic acid sequence encoding the polypeptide of interest may be made to generate a nucleic acid encoding a target sequence without substantially affecting the function of the polypeptide of interest.

Site-specific and region-directed mutagenesis techniques, as well as standard recombinant techniques can be employed for generating some of the nucleic acid sequences that encode the polypeptides used in the invention. See Current Protocols in Molecular Biology, Vol. 1, Ch. 8 (Ausubel et al., eds., J. Wiley & Sons 1989 & Supp. 1990–93); Protein Engineering (Oxender & Fox eds., A. Liss, Inc. 1987). In addition, linker-scanning and PCR-mediated techniques can be employed for mutagenesis. See PCR Technology (Erlich ed., Stockton Press 1989); Current Protocols in Molecular Biology, Vols. 1 & 2, supra.

The vector may also contain any number of regulatory elements for driving expression of the polypeptides. Nucleic acid sequences encoding polypeptides may be operatively associated with a regulatory element. Regulatory elements include, but are not limited to, inducible and non-inducible promoters, enhancers, operators and other elements that drive or otherwise regulate gene expression.

Typically, a nucleic acid sequence encoding a polypeptide is operatively linked to a promoter that is active in the appropriate environment, i.e. a host cell. A variety of appropriate promoters are known in the art and may be used in the present invention. The promoter may be a promoter that naturally drives expression of the carrier polypeptide. The promoter may be a viral promoter, a bacterial promoter, a yeast promoter, insect promoter or a plant promoter, and can be host cell-specific. Examples of promoters include, without limitation, T7, metallothionein I, or polyhedron promoters. For example, if the polypeptides will be expressed in a bacterial system, inducible promoters such as pL of bacteriophage gamma, placZ, ptrp, ptac (trp-lac hybrid promoter) and the like may be used. In mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used.

Plant promoters useful in the invention include both natural constitutive and inducible promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett et al., *Proc. Natl. Acad. Sci. U.S.A.* 90:4567, 1993); In2-1 and In2-2 regulator sequences which are activated by substituted benzenesulfonamides, e.g., herbicide safeners (Hershey et al., *Plant Mol. Biol.* 17:679, 1991); and the GRE regulatory sequences which are induced by glucocorticoids (Schena et al., *Proc. Natl. Acad. Sci. U.S.A.* 88:10421, 1991) (See Example 10). Other suitable plant promoters include, but are not limited to, the 35S RNA and 19S RNA promoters of CaMV (Brisson et al., *Nature* 310:511, 1984; Odell et al., *Nature* 313:810, 1985); the full-length transcript promoter from Figwort Mosaic Virus (FMV) (Gowda et al., *J. Cell Biochem.* 13D:301, 1989) and the coat protein promoter to TMV (Takamatsu et al, *EMBO J.* 6:307, 1987). Alternatively, plant promoters such as the light-inducible promoter from the small subunit of ribulose bis-phosphate carboxylase (ssRUBISCO) (Coruzzi et al., *EMBO J.* 3:1671, 1984; Broglie et al., *Science* 224:838, 1984); mannopine synthase promoter (Velten et al., *EMBO J.* 3:2723, 1984) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley et al., *Mol. Cell. Biol.* 6:559, 1986; Severin et al., *Plant Mol. Biol.*, 1:827, 1990) may be used.

Yeast promoters useful in the invention include both natural constitutive and inducible promoters as well as engineered promoters. Suitable native yeast promoters include, but are not limited to the wild-type α-factor promoter, as well as other yeast promoters. Preferably the promoter is selected from the list including promoters for the glycolytic enzymes phosphoglucoisomerase, phosphofructokinase, phosphotrioseisomerase, phosphoglucomutase, enolase, pyruvate kinase (PyK), glyceraldehyde-3-phosphate dehydrogenase (GAP or GAPDH), alcohol dehydrogenase (ADH) (EPO Publication No. 284,044). See, for example, EPO Publication Nos. 120,551 and 164,556.

Synthetic hybrid promoters consisting of the upstream activator sequence of one yeast promoter, which allows for inducible expression, and the transcription activation region of another yeast promoter also serve as functional promoters in a yeast host. Examples of hybrid promoters include ADH/GAP, where the inducible region of the ADH promoter is combined with the activation region of the GAP promoter (U.S. Pat. Nos. 4,876,197 and 4,880,734). Other hybrid promoters using upstream activator sequences of either the ADH2, GAL4, GAL10, or PHO5 genes combined with the transcriptional activation region of a glycolytic enzyme such as GAP or PyK are available in the art (EPO Publication No. 164,556). More preferably the yeast promoter is the inducible ADWPGAP hybrid promoter.

Yeast-recognized promoters also include naturally occurring non-yeast promoters that bind yeast RNA polymerase and initiate translation of the coding sequence. Such promoters are available in the art. See, for example, Cohen et al. (1980) Proc. Natl. Acad. Sci. USA 77:1078; Mercereau-Puigalon et al. (1980) Gene 11:163; Panthier et al. (1980) Curr. Genet. 2:109); Henikoff et al. (1981) Nature 283:835; and Hollenberg et al. (1981) Curr. Topics Microbiol. Immunol. 96:119; herein incorporated by reference.

Promoters produced by recombinant DNA or synthetic techniques may also be used. Other promoters, both constitutive and inducible will be known to those of skill in the art.

The vector may also include enhancer sequences. Enhancer sequences can be placed in a variety of locations in relation to polypeptide-encoding nucleic acid sequences. For example, enhancer sequences can be placed upstream or downstream of the coding sequences, and can be located adjacent to, or at a distance from, the polypeptide encoding nucleic acid sequences.

The vector may also contain a nucleic acid sequence encoding a selectable marker for use in identifying host cells containing a vector. A selectable marker in a vector typically confers some form of drug or antibiotic resistance to the host cells carrying the vector.

A number of selection systems may be used. In bacterial host cells, a number of antibiotic markers may be used. Antibiotic markers include tetracycline, ampicillin, and kanamycin. In mammalian host cells, selections systems include, but are not limited to herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48: 2026), and adenine phosphoribosyltransferase (Lowy, et al., 1980, Cell 22: 817). Also, antimetabolite resistance can be used as the basis of selection for dhfr, which confers resistance to methotrexate (Wigler, et al., 1980, Proc. Natl. Acad. Sci. USA 77: 3567; O'Hare, et al., 1981, Proc. Natl. Acad. Sci. USA 78: 1527); gpt, which confers resistance to mycophenolic acid (Mulligan & Berg, 1981, Proc. Natl. Acad. Sci. USA 78:2072; neo, which confers resistance to the aminoglycoside G418 (Colberre-Garapin, et al., 1981, J. Mol. Biol. 150: 1); and hygro, which confers resistance to hygromycin (Santerre, et al., 1984, Gene 30: 147) genes. Additional selectable genes include, trpB, which allows cells to utilize indole in place of tryptophan; hisD, which allows cells to utilize histinol in place of histidine (Harman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

Depending on the host cell and the vector system utilized, any of a number of suitable transcription and translation elements, including constitutive and inducible promoters, transcription enhancer elements, transcription terminators, etc. may be used in the expression vector (see e.g., Bitter et al., 1987, Methods in Enzymology, 153:516–544) as described earlier. Selection of the appropriate transcription and translation elements are readily apparent to a person of ordinary skill in the art.

Vectors based on bovine papilloma virus which have the ability to replicate as extrachromosomal elements may be of particular interest (Sarver et al., 1981, Mol. Cell. Biol. 1:486). Shortly after entry of this DNA, the plasmid replicates to about 100 to 200 copies per cell. Transcription of the polypeptide encoding nucleic acid sequences does not require integration of the plasmid into the host's chromosome, thereby yielding a high level of expression. These vectors can be used for stable expression by including a selectable marker in the plasmid, such as, for example, the neo gene.

Factors of importance in selecting a particular expression system include: the ease with which a host cell that contains the vector may be recognized and selected from a host cell that does not contain the vector; the number of copies of the vector which are desired in a particular host cell; and whether it is desirable to be able to "shuttle" the vector between different types of host cells.

In one embodiment of the invention, a polypeptide that is labeled with a FlAsH target sequence motif, is produced using a DNA construct of the invention. The DNA construct, referred to as a FlAsH tag vector, is constructed such that it contains an origin of replication, a selectable marker, a promoter that allows expression of the polypeptide of interest in an appropriate cell type, and a multiple cloning site, wherein at the 5' end of the multiple cloning site is a FlAsH target sequence motif.

In another embodiment of the invention, a polypeptide that is labeled with a genetically encoded affinity tag and the FlAsH target sequence motif, is produced using a DNA construct of the invention. The DNA construct, referred to as a dual affinity tag vector, is constructed such that it contains an origin of replication, a selectable marker, a promoter that allows expression of the polypeptide of interest, and a multiple cloning site, wherein at the 5' end of the multiple cloning site is a genetically-encoded affinity tag, and wherein at the 3' end of the cloning site there is a FlAsH target sequence motif.

Another embodiment of the invention is a DNA construct as described above except the FlAsH target sequence motif is placed at the 5' end of the multiple cloning site, and the genetically encoded affinity tag is placed at the 3' end of the multiple cloning site.

In another embodiment, a genetically-encoded affinity tag is selected from the group consisting of polyhistidine, maltose binding protein, glutathione S-transferase, and the Flag tag. In a preferred embodiment the polyhistidine tag is the 6×-histidine tag (His6).

One embodiment of the invention includes DNA constructs of the invention designed such that the origin of replication, selectable marker, and promoter function in a prokaryotic cell host.

Another embodiment of the invention includes DNA constructs of the invention designed such that the origin of replication, selectable marker, and promoter function in a eukaryotic cell host.

Still another embodiment of the invention includes DNA constructs of the invention designed such that the origin of replication, selectable marker, and promoter function in a plant cell host.

And yet another embodiment of the invention includes DNA constructs of the invention designed such that the origin of replication, selectable marker, and promoter function in an insect cell host.

In another aspect, the invention provides a kit containing a modified FlAsH compound of the invention, e.g., Formula I. The kit may include instructions and materials for producing the above mentioned modified bis-arsenical FlAsH compound; immobilizing the modified bis-arsenical FlAsH compound to a solid support; producing the polypeptide of interest which contains the FlAsH target motif; contacting a sample containing the polypeptide of interest with the FlAsH compound immobilized to a solid support; and/or eluting the polypeptide of interest from the immobilized FlAsH compound in substantially pure form using a single purification step.

In a preferred embodiment, the kit contains a FlAsH compound modified by acylation with an amino acid (i.e., Formula I). The kit may also contain a solid support on which the acylated FlAsH compound is immobilized. A solid support included in the kit maybe selected from the group consisting of agarose, polyacrylimide, glass, ceramics, natural or synthetic polymeric materials, beads, coverslips, paper, metals, metalloids, polacryloylmorpholide, various plastics and plastic copolymers such as Nylon™, Teflon™, polyethylene, polypropylene, poly(4-methylbutene), polystyrene, polystyrene/latex, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and controlled-pore glass (Controlled Pore Glass, Inc., Fairfield, N.J.), aerogels (see e.g., Ruben et al., J. Materials Science 27, 4341–4349 (1992); Rao et al., J. Materials Science 28, 3021 (1993); Back et al., J. Phys. D. Appl. Phys. 22, 7309 (1989); Kim and Jang, J. Am Ceram. Soc. 74, 1987–1992 (1991)), affinity exchange resins, and other materials generally known to one skilled in the art to be suitable for use in affinity columns. In a preferred embodiment, the β-alanyl FlAsH is reacted with N hydroxysuccinamide (NHS)-functionalized agarose beads.

The kit may contain a modified FlAsH compound previously immobilized to a solid support and pre-packaged for column chromatography. The column can be pre-packaged for a type of chromatography selected from the group consisting of, but not limited to, batch chromatography, FPLC, HPLC, affinity chromatography and gel filtration.

The kit may also contain a dithiol solution for eluting the polypeptide of interest from the FlAsH compound. In one aspect, the kit may contain the dithiol 1,2 Ethanedithiol (EDT) or the dithiol, dithiolthreitol (DTT), or the dithiol, 2,3 Dimercaptopropanesulfonate (DMPS), for example.

Another aspect of the invention is another kit designed for use with dual affinity tag labeled proteins. The kit may include instructions and materials needed for producing the above mentioned modified bis-arsenical FlAsH compound; immobilizing the modified bis-arsenical FlAsH compound to a solid support; immobilizing a second molecule to a separate solid support; producing the polypeptide of interest which contains both the FlAsH target motif and the second genetically-encoded affinity tag; contacting the sample containing the polypeptide of interest with the FlAsH compound immobilized to a solid support; eluting the polypeptide of interest from the immobilized FlAsH compound; contacting the sample containing the polypeptide of interest with the second compound or molecule immobilized to a solid support; and/or eluting the polypeptide of interest from the second affinity compound in substantially pure form using a two step purification process.

In a preferred embodiment, the kit contains a FlAsH compound modified by acylation with an amino acid. The second affinity compound can be immobilized using techniques known to those of skill in the art. The kit also contains a solid support on which to immobilize either the acylated FlAsH compound, or the second affinity compound. The solid support included in the kit maybe selected from agarose, polyacrylimide, glass, ceramics, natural or synthetic polymeric materials, beads, coverslips, paper, metals, metalloids, polacryloylmorpholide, various plastics and plastic copolymers such as Nylon™, Teflon™, polyethylene, polypropylene, poly(4-methylbutene), polystyrene, polystyrene, polystyrene/latex, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and controlled-pore glass (Controlled Pore Glass, Inc., Fairfield, N.J.), aerogels (see e.g., Ruben et al., J. Materials Science 27, 43414349 (1992); Rao et al., J. Materials Science 28, 3021 (1993); Back et al., J. Phys. D. Appl. Phys. 22, 7309 (1989); Kim and Jang, J. Am Ceram. Soc. 74, 1987–1992 (1991)), affinity exchange resins, and other materials generally known to one skilled in the art to be suitable for use in affinity columns. In a preferred embodiment, the β-alanyl FlAsH is reacted with N hydroxysuccinamide (NHS)-functionalized agarose beads.

In another aspect, the kit may include a second affinity compound such as polyhistidine, maltose binding protein, glutathione S-transferase, and the Flag tag, for example. In a preferred embodiment the polyhistidine tag is the 6x-histidine tag (His6).

The kit may also contain the FlAsH compound and the second affinity compound, already immobilized to a solid support and pre-packaged for column chromatography. The column can be pre-packaged for a type of chromatography selected from the group consisting of, but not limited to, batch chromatography, FPLC, HPLC, affinity chromatography and gel filtration.

The kit may also contain a dithiol solution for eluting the polypeptide of interest from the FlAsH compound, and a reagent appropriate for eluting the polypeptide of interest from the second immobilized affinity compound. The kit may contain 1,2 Ethanedithiol (EDT), dithiolthreitol (DTT), or 2,3 Dimercaptopropanesulfonate (DMPS), for example. One of skill in the art will know the appropriate reagents for eluting the polypeptide of interest from the second affinity compound. For example, the kit may include a low pH solution to elute the polypeptide of interest from the polyhistidine affinity tag. Further, the kit may include a solution of imadizole to elute the polypeptide of interest from the polyhistidine affinity tag.

The modified bis-arsenical molecule, in combination with the target sequence, form a bis-arsenical molecule/target sequence complex that is useful in a number of methods. The complex is particularly useful in methods for labeling a polypeptide of interest. The polypeptide of interest can be associated with the target sequence to form a bonding partner. The bonding partner may be produced by any method, including a number of the above-described methods.

A polypeptide of interest that includes a target sequence is contacted with the modified bis-arsenical molecule. Contact of the modified bis-arsenical molecule with the polypeptide of interest is performed under conditions appropriate for a specific reaction to occur between the modified bis-arsenical molecule and the target sequence to form the bis-arsenical molecule/target sequence complex.

A modified bis-arsenical molecule/target sequence complex that generates a detectable signal may be used if detection of a labeled carrier molecule is desired. A particular advantage of using the modified bis-arsenical molecule and the target sequence for labeling is the specificity and the reversibility of the interaction. The bis-arsenical molecule/target sequence complex may be dissociated, for example, after the detection of the complex.

The modified bis-arsenical molecule may be added to a composition that includes the target sequence. The bis-arsenical molecule may or may not be capable of traversing a membrane. The bonding partner may be, for example, in a test tube, a microtiter well or immobilized on a solid phase. Uses of the bis-arsenical molecule/target sequence complex include polypeptide purification, immunoassays, and other biological and chemical assays.

Immobilization of either the modified bis-arsenical molecule or the polypeptide of interest to a solid phase may be particularly useful. Immobilization may include adsorption, absorption or covalent bonding. A solid phase may be inert or it may be reactive for coupling. Solid phases that may be used include agarose, polyacrylimide, glass, ceramics, natural or synthetic polymeric materials, beads, coverslips, paper, metals, metalloids, polacryloylmorpholide, various plastics and plastic copolymers such as Nylon™, Teflon™, polyethylene, polypropylene, poly(4-methylbutene), polystyrene, polystyrene, polystyrene/latex, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and controlled-pore glass (Controlled Pore Glass, Inc., Fairfield, N.J.), aerogels (see e.g., Ruben et al., J. Materials Science 27, 4341–4349 (1992); Rao et al., J. Materials Science 28, 3021 (1993); Back et al., J. Phys. D. Appl. Phys. 22, 7309 (1989); Kim and Jang, J. Am Ceram. Soc. 74, 1987–1992 (1991)), affinity exchange resins, and other materials generally known to one skilled in the art to be suitable for use in affinity columns.

The invention will be further understood with reference to the following examples, which are purely exemplary, and should not be taken as limiting the true scope of the present invention as described in the claims.

EXAMPLES

Example 1

Synthesis of 4',5'-Bis(1,2,3-Dithioarsolan-2yl)5((5-Aminoethyl)Aminocarbonyl)Fluorescein Fmoc-β-alanine was purchased from Novabiochem. All other starting materials were purchased from Aldrich chemical company. Thin layer chromatography (TLC) was carried out using Baker-flex silica gel plates with fluorescent indicator (245 nm). FlAsH chromatography was performed on Beakers Silica gel for flash chromatography purchased from VWR. MALDI-MS analysis was performed using a Voyager-DE (PerSeptive Biosystems) with a gentistic acid matrix (Sigma). Elemental analysis was performed by S.F Analytical Laboratories.

5((5FMOC-Aminoethyl)Aminocarbonyl)Fluorescein (2)

Dicyclohexylcarbodiimide (4 mmol, 827 mg) was added to Fmoc-β-alanine (3.5 mmol, 1.1 g) dissolved in 0.4 ml of DMF. 4-amino fluorescein (0.5 mmol, 174 mg) dissolved in 0.7 ml of DMF was added to the mixture. The mixture was stirred overnight at room temperature. The next day the mixture was centrifuged and the precipitate was separated. The supernatant was evaporated to dryness using a rotovap and the residue was dissolved in hexane. The product was purified twice by flash chromatography using 3:7 cyclohexane ethylacetate ($R_f$=0.64). Yield: 0.135 mmol (26%), $_{max}$=499 nm, m/z=420 (theoretical m+H$^+$=419).

5((5-Aminoethyl)Aminocarbonyl)Fluorescein (3)

Dry piperidine (0.65 mmol) was added to 0.135 mmol of 5-((5-Fmoc-aminoethyl)aminocarbonyl)fluorescein dissolved in 2.6 ml of DMF. The mixture turned red immediately. The progress of the reaction was monitored by TLC in cyclohexane:ethylacetate 3:7. The reaction was stirred for 2 hr at room temperature, evaporated to dryness, and the product precipitated by addition of ether. The red precipitate was washed with ether several times and dried. Yield: 0.09 mmol (13.8%); Hg=42.4% by weight (theoretical value 42.73%).

4',5'-Bis(Acetoxymercuri)-5-((5-Aminoethyl)Aminocarbonyl)Fluorescein (4)

5-((5-aminoethyl)aminocarbonyl)fluorescein (0:09 mmol) was dissolved in 15 ml of 2% acetic acid and 6.5 ml of ethanol and warmed to 50° C. Mercuric acetate (0.2 mmoles, 51.8 mg) dissolved in 0.65 ml of acetic acid was added dropwise to the flourescein solution. The reaction mixture was left at 50° C. for 1 hr and then at room temperature overnight. The light orange solution turned pale yellow after 10 min and red after 2 hr. The next day a red precipitate was obtained and the mixture was evaporated to dryness. The precipitate was washed with a total of 35 ml of water in 5 portions to remove excess mercuric acetate. Yield: 0.08 mmol, $\lambda_{max}$=505 nm.

4',5'-Bis(1,2,3-Dithioarsolan-2yl)5-((5-Aminoethyl)Aminocarbonyl)Fluorescein (5)

The above mercuric derivative (0.043 mmol, 40 mg) was placed in a 25 ml two neck flask equipped with a cooling condenser. N-methylpyrrolidinone (0.6 ml), diisopropyl-ethylamine (0.032 ml, 0.346 mmol), AsCl$_3$ (0.075 ml, 0.87 mmol), and a catalytic amount of palladium acetate were added. After one hour the mixture turned to a clear orange-red solution. The mixture was left overnight and then quenched by the addition of 0.09 ml ethanedithiol and 15 ml of 2 M MOPS at pH 7. The resulting yellow precipitate was removed by centrifugation and the solution which contains the product was used in this form.

This product was also purified using a spehasil peptide C85um ST 4.6/100 HPLC column (Pharmacia) using a 20–90% DMF/1 mM phosphate (pH 7.0) gradient. The pink product (β-alanyl FlAsH) eluted at 95% DME. The product has an absorption maxima of 508 nm and gives a 20-fold fluorescence enahancement on incubation with the FlAsH-tag peptide (WEAAAREACCRECCARA, SEQ ID NO: 2; synthesized by the HHMI peptide synthesis facility and used without purification). For some experiments, the product was purified in a similar fashion using low pressure chromatography on hydrophobic substituted sepharose. Matrix-assisted laser desorption ionization mass spectrometry gave a mass of 753 (theoretical m+H$^+$ 752).

The final compound was coupled to Affigel-10 or -15 (Biorad) or to HiTrap-NHS columns (Amersham-Pharmacia) at 3 µmol/ml resin. Binding was done in an isopropanol/DMF/water mixture for 1–2 hr at room temperature. The resin was then washed with several volumes of isopropanol and unreacted NHS groups were quenched by incubation with 1 M ethanolamine in isopropanol for 30 minutes. Coupling was followed by absorbance; typically greater than 90% coupling was achieved. The resulting resin were then washed with several volumes of buffer and stored in 1 mM DTT in isopropanol until use.

Example 2

Proteins and Assays

Constructs encoding K339FlAsH and K560FlAsH were prepared by using polymerase chain reaction to replace the GFP sequence in constructs K560GFP (Case, et al., The directional preference of kinesin motors is specified by an element outside of the motor catalytic domain. Cell 90:959–966 (1997)) and K339GFP with the FlAsH-tag sequence (WEAAAREACCRECCARA, SEQ ID NO: 2). Bacterial high speed supernatants were prepared essentially as described in (Case, et al., Cell 90:959–966 (1997), except that cell lysis was performed with a Microfluidizer 110S (Microfluidics Corp.) The supernatants were frozen in liquid nitrogen and stored at −80° C. until needed. Microtubule gliding assays were performed as described for untagged kinesins (Case, et al., Cell 90:959–966 (1997)). Protein quantitation was performed by densitometry of coomasie-stained SDS-PAGE gels using BSA as a standard. Gel filtration was performed on a Superose 6 PC 3.2/30 column in 25 mM PIPES pH 6.8, 200 mM NaCl, 2 mM MgCl$_2$, and 1 mM EGTA. MALDI-MS analysis was performed using a Voyager-DE (PerSeptive Biosystems) with a sinapinic acid matrix (Sigma).

Purification

Batch purification was performed by incubating 100 µl of FlAsH resin with 1 mL of bacterial high speed supernatant for 1 hr at 4° C. with end-over-end rotation. The FlAsH resin was then pelleted and washed 4×1 ml with wash buffer (80 mM PIPES pH 6.8, 2 MM MgCl$_2$, 1 mM EGTA, 5 mM γ-mercaptoethanol, 0.1 mM DTT). The specifically bound protein was then eluted 5×200 µl with 50 mM DTT in wash buffer. Each elution was incubated for 5 min to allow equilibration.

Column purification was performed by loading 20 ml of bacterial high speed supernatant onto a 1 ml FlAsH column at 0.5 ml/min. The column was washed with buffer A (25 mM PIPES, 2 mM MgCl$_2$, 1 mM EGTA, 0.1 mM ATP, 5 mM β-ME) until the A$_{280}$ returned to baseline. The column was then washed 3×2 ml with 1 mM DTT in buffer A with 5 min pauses between each wash to allow equilibration. Protein was then eluted with 50 mM DTT in buffer A 5×2 ml with 5 min pauses. Elution with 2,3-dimercaptopropanesulfonate was performed in the same manner except that 10-fold lower concentrations of DMPS were used.

Purification of Kinesin by Flash Affinity Chromatography

To test the FlAsH affinity purification, we prepared kinesin constructs C-terminally tagged with the peptide WEAAAREACCRECCARA (SEQ ID NO: 2). This peptide specifically chelates FlAsH via the four cysteines. We chose kinesin as our test protein because it is easily tested for activity by microtubule gliding. We prepared both a monomeric construct, encoding the first 339 residues of human conventional kinesin (K339FL), and a dimeric construct encoding the first 560 residues (K560FL). The introduction of this peptide tag on the C-terminus of K560 did not change either the expression level or the solubility of the protein when expressed in *E. coli* as compared to an identical construct with a C-terminal 6×His tag. Thus, the C-C-$X_1$-$X_2$-C-C (SEQ ID NO: 1) tag does not impair protein solubility or expression.

Incubation of high-speed supernatant from *E. coli* expressing K339FL followed by batch elution with 1,2-ethanedithiol (EDT) resulted in a major product (90% pure) that was the tagged kinesin. 1 ml of *E. coli* high-speed supernatant was bound to 0.1 ml of FlAsH beads and incubated for 1 hr. After three 1 ml batch washes, the tagged protein was eluted by incubation with 12 mM EDT.

Purification of K339FL using DTT as the eluant. Beads were incubated in 1 ml of *E. coli* high speed supernatent, then washed five times with 1 ml of buffer containing 0. 1 mM DTT. Protein was then eluted by five 0.2 ml batch washes with buffer plus 50 mM DTT. The eluted protein was much purer than a control 6×His tagged protein (K339GFP-6×His).

K339GFP-6×His was purified by metal affinity chromatography. This protein was expressed and lysed under the same conditions as K339FL, bound to 1 ml NiNTA resin (Qiagen). The resin was washed with 20 ml wash buffer (pH 6.0 phosphate, 250 mM NaCl), and then eluted with pH 8.0 phosphate, 500 mM imidazole.

The single band that contaminates this protein is not a kinesin degradation product, as determined by immunoblotting, but was not consistently found in our FlAsH purifications. Despite the presence of this single contaminant, the protein is much purer than a similar polyhistidine tagged protein (K339GFP6×His) purified by NiNTA affinity chromatography. Experiments performed with a FlAsH column (rather than in batch) with more extensive washing gave improved protein purity. The resin capacity was determined by coupling known amounts of purified FlAsH compound to the affinity resin and determining the amount of protein which could be purified. The yield of tagged protein was 10% of the bound FlAsH compound.

Mass spectrometry of the purified K339FL showed a single peak of molecular weight 39765 (expected: 39770) and no higher molecular weight peaks, indicating that the K339FL is not forming covalent complexes. Purified K339FL eluted on a gel filtration column as a single peak at the same volume as comparable monomeric kinesins. This demonstrates that the addition of the tag does not cause aggregation of K339FL in solution.

We also tested kinesin eluted from the FlAsH column for activity, without dialysis or buffer exchange. K560FL purified by FlAsH-affinity chromatography was fully active in microtubule gliding assays (29.8±6.3 µm/min vs. 24.3±9.4

µm/min for K560GFP), consistent with previously observed values (Case, et al., 1997; Woehlke, et al., 1997). In contrast, small amounts of $Ni^{2+}$ displaced from metal affinty columns has been found to inhibit kinesin activity. FlAsH should remain on the column matrix, as it is covalently bound.

In initial purification experiments, 1,2-ethanedithiol (EDT) was used to elute the specifically bound protein. However, EDT has an extremely unpleasant smell and it oxidizes and aggregates with the tagged protein after an overnight incubation in aqueous solution, leading to a loss of protein. To avoid these problems, we tested two other dithiol elution agents: dithiothreitol (DTT) and 2,3-dimercaptopropanesulfonate (DMPS). Although not as efficient as EDT at low concentrations, 50 mM DTT completely eluted the bound protein (FIG. 2). With DTT elution, the protein showed no oxidation or aggregation problems. Similarly, DMPS, which eluted protein from the FlAsH column at the same concentrations as EDT, did not cause precipitation on prolonged incubation and is odor-free.

It will be apparent to those skilled in the art that various modifications and variations can be made to the compounds and processes of this invention. Thus, it is intended that the present invention cover such modifications and variations, provided they come within the scope of the appended claims and their equivalents. Accordingly, the invention is limited only by the following claims.

What is claimed is:

1. A method for isolating a polypeptide of interest comprising:
   a) contacting a modified Fluorescein arsenical helix binder (FlAsH) compound, which has been modified by acylation with an amino acid, and immobilized on a solid support, with a solution containing a polypeptide of interest, which has been modified to contain a FlAsH target sequence motif, under conditions that allow binding of the polypeptide to the immobilized FlAsH compound; and
   b) eluting and recovering the polypeptide of interest from the immobilized FlAsH compound.

2. The method of claim 1, wherein the modification is by acylation with β-Alanine.

3. The method of claim 1, wherein the polypeptide of interest has been modified by the addition of the FlAsH target sequence motif C-C-$X_1$-$X_2$-C-C (SEQ ID NO: 1), where $X_1$ and $X_2$ are any amino acid.

4. The method of claim 3 wherein $X_1$ and $X_2$ are the same amino acid.

5. The method of claim 3 wherein $X_1$ and $X_2$ are different amino acids.

6. The method of claim 3 wherein the sequence motif has been added at either the N terminus or C terminus of the polypeptide, or in an alpha-helical region of the polypeptide.

7. The method of claim 1, wherein said solid support is selected from the group consisting of agarose, polyacrylamide, glass, ceramics, natural or synthetic polymeric materials, beads, cover slips, paper, metals, metalloids, polyacryloylmorpholide, polyamide, poly(tetrafluoroethylene), polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and controlled-pore glass, aerogels, and affinity exchange resins.

8. The method of claim 1, wherein the polypeptide of interest is eluted from the immobilized FlAsH compound using a dithiol solution.

9. The method of claim 8, where the dithiol solution is selected from the group consisting of 1,2-Ethanedithiol (EDT), dithiothreitol (DTT), and 2,3-Dimercaptopropanesulfonate (DMPS).

10. The method of claim 1, wherein said solution which contains the polypeptide of interest is selected from the group consisting of cell lysate, crude polypeptide extract, and partially purified polypeptide extract.

11. The method of claim 10, wherein said solution is obtained from a cell or cell free solution derived from the group consisting of a plant, a prokaryote, and a eukaryote.

12. The method of claim 1, wherein the modified FlAsH compound comprises 4'5'-bis(1,2,3-dithioarsolan-2-yl)5 (5-aminoethyl)aminocarbonyl-fluorescein.

13. The method of claim 1, wherein the modified FlAsH compound is immobilized on a solid support by reaction with an N-hydroxysuccinamide (NHS) functionalized solid support.

14. The method of claim 1, wherein the modified FlAsH compound has been modified at a primary amine of a 5 position of flourescein, by acylation with an amino acid.

15. A method for isolating a polypeptide of interest comprising;
   a) contacting a modified Fluorescein arsenical helix binder (FlAsH) compound, which has been modified by acylation with an amino acid, immobilized on a solid support, with a solution containing a polypeptide of interest, which has been modified to contain a FlAsH target sequence motif, under conditions that allow binding of the polypeptide to the immobilized FlAsH compound, wherein the solid support is selected from the group consisting of agarose, polyacrylamide, glass, ceramics, natural or synthetic polymeric materials, beads, cover slips, paper, metals, metalloids, polyacryloylmorpholide, polyamide, poly(tetrafluoroethylene), polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and controlled-pore glass, aerogels, and affinity exchange resins; and
   b) eluting and recovering the polypeptide of interest from the immobilized FlAsH compound.

16. The method of claim 15, wherein the modification is by acylation with β-alanine.

17. The method of claim 15, wherein the modified FlAsH compound is immobilized on a solid support by reaction with an N-hydroxysuccinamide (NHS) functionalized solid support.

18. The method of claim 17, wherein the NHS functionalized solid support comprises NHS functionalized agarose beads.

19. The method of claim 15, wherein the modified FlAsH ound comprises 4'5'-bis(1,2,3-dithioarsolan-2-yl)5(5-aminoethyl)aminocarbonyl-flourescein.

* * * * *

UNITED STATES PATENT AND TRADEMARK OFFICE
CERTIFICATE OF CORRECTION

PATENT NO. : 6,831,160 B1
DATED : December 14, 2004
INVENTOR(S) : Vale et al.

It is certified that error appears in the above-identified patent and that said Letters Patent is hereby corrected as shown below:

Title page,
Item [75], Inventors, delete "Marija Matsuka" and replace with -- Marija Matuska --

Signed and Sealed this

Twenty-first Day of June, 2005

JON W. DUDAS
*Director of the United States Patent and Trademark Office*